United States Patent [19]

Hallisy et al.

[11] Patent Number: 5,349,091
[45] Date of Patent: Sep. 20, 1994

[54] PROCESS FOR RECYCLING CURED POLYSULFIDE SEALANTS

[75] Inventors: Michael J. Hallisy, Woodstock; John R. Gilmore, Crystal Lake; Steven J. Hobbs, Woodstock; Warren G. Duncan, Crystal Lake, all of Ill.

[73] Assignee: Morton International, Inc., Chicago, Ill.

[21] Appl. No.: 53,642

[22] Filed: Apr. 27, 1993

[51] Int. Cl.$^5$ ............... C07C 321/14; C07C 321/12
[52] U.S. Cl. ........................................ 568/22; 568/21
[58] Field of Search ............................. 568/21, 22

[56] References Cited

U.S. PATENT DOCUMENTS

| | | | |
|---|---|---|---|
| 2,415,449 | 2/1947 | Sverdrup et al. | 260/720 |
| 3,770,678 | 11/1973 | Paul, 3rd. | 260/28 |
| 4,425,389 | 1/1984 | Schollhorn et al. | 428/34 |
| 4,675,126 | 6/1987 | Unger et al. | 252/153 |

*Primary Examiner*—Johann Richter
*Assistant Examiner*—Margaret J. Page
*Attorney, Agent, or Firm*—Robert M. Didrick; Gerald K. White

[57] ABSTRACT

Solid waste materials comprising oxidatively-cured, solid polysulfide sealants containing spent oxidant, fillers, plasticizers, and other formulating aids are reverted to a liquid sealant comprising mercaptan-terminated polysulfides by reducing them with a liquid mercaptan-terminated polysulfide at temperatures ranging from about 50° to about 110° C. Upon the addition of fresh curing agent and recuring, the reclaimed sealant has satisfactory tensile strength and elongation properties.

5 Claims, No Drawings

PROCESS FOR RECYCLING CURED POLYSULFIDE SEALANTS

BACKGROUND OF THE INVENTION

This invention relates to the reclamation of cured polysulfide sealants. More particularly, it relates to the reversion of the cured sealant to the liquid polysulfide and the recycling of the product. Still more particularly, it relates to the reduction of the cured polysulfide by heating it with a mercaptan-terminated liquid polysulfide.

More than 95% of all polysulfide polymers are made by the reaction of sodium polysulfide with bis(chloroethyl) formal and small proportions of 1,2,3-trichloropropane, which provides branching sites for crosslinking during a subsequent curing step. In general, the principal reactions that take place may be summarized by the equations:

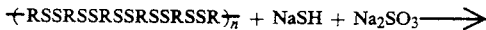

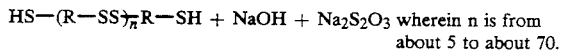

wherein n is from about 5 to about 70.

The preparation of the polysulfides is described by E. R. Bertozzi in *Macromolecular Syntheses*, p.35, Vol. 7, E. M. Fettes, ed., John Wiley & Sons, Inc., New York, (1979).

Solid polysulfide elastomers having terminal thiol groups and a molecular weight of about 80,000 (n is from about 300 to 1000) may be cured by oxidation to give products used in printing rolls, paint-spray hose, solvent hose, gaskets, and gas meter diaphragms. Liquid polysulfide polymers, on the other hand, also have terminal thiol groups but their molecular weight is much lower, i.e. from about 400 to about 8000 (n is from about 6 to 50). These liquid polysulfides are cured in place at the site of their use, which is mainly as sealants for double-pane insulating windows, in other building construction, for boat hulls and decks, for aircraft integral fuel tanks, and in aircraft construction.

Waste material comprising scraps of cured polysulfide sealants generated by large scale applicators of aircraft, window, and industrial grade sealants is fast losing a place to be dumped. The cost of landfill cells is continuously escalating. Some landfill operators are beginning to refuse such sealants because of their heavy metal content. Manufacturers of the liquid polysulfides that are precursors to the cured sealants are beginning to search for ways to alleviate the disposal problems faced by their customers.

Hydrogen sulfide at rather low concentrations is known to attack cured polysulfides and cause the surface to soften. Hydrogen sulfide is, however, a very dangerous poisonous gas. It would be preferable, moreover, to cause the cured material to change into a liquid usable once again as a sealant curable by an oxidative process.

The problem of reclaiming vulcanized rubber from scrap material was addressed by Sverdrup et. al. in U.S. Pat. No. 2,415,449 wherein it is taught that a mixture of ground scrap and up to 7% by weight of a reclaiming agent, i.e., an oxygen carrier, is treated at greater than 100° C. under conditions such that oxygen is available, either from the agent, the atmosphere, or elsewhere. A reversible plasticity is achieved rapidly and the treatment is stopped by, for example, removing the reclaiming agent to avoid reversion. Mercaptans, organic sulfides, terpenes, and unsaturated ketones are named as the oxygen carrying reclaiming agent, i.e., one which is capable of reversible oxidation and reduction.

U.S. Pat. No. 4,425,389 (Schöllhorn et. al.) teaches that by mixing solid mercaptoterminal polysulfide polymers with from 5 to 15% by weight of liquid mercaptoterminal polysulfide polymers, one can produce sealing compositions which remain soft at 50° to 100° C. to such a point that they may be pumped and easily sprayed, even though a hardening agent is present.

There remains a need for a method for reverting a cured polysulfide sealant to a liquid, recurable state so that the sealant may be recycled in such manner over and over again, thus reducing the demand for scarce landfill space.

SUMMARY OF THE INVENTION

It is an object of this invention, therefore, to provide a method for reducing the sulfide linkages in an oxidatively-cured polysulfide whereby the solid is converted into a liquid mercaptanterminated polysulfide.

It is related object of this invention to provide a method for the reclamation and recycling of oxidatively-cured polysulfide sealants containing residual manganese oxide-based curing agents and various conventional fillers and additives.

It is another related object of this invention to provide reverted polysulfide sealants for re-use in the sealant industry.

These and other objects of this invention which shall become apparent from the following description thereof are provided by the method comprising reacting an oxidatively cured sealant in a nonaqueous system at a temperature of from about 50° C. to about 110° C. with an amount of a mercapto group-terminated liquid polysulfide sufficient to provide from about 1.0% to about 3% by weight of mercapto groups in the reclaimed sealant.

DESCRIPTION OF THE PREFERRED EMBODIMENTS

The mercapto group-terminated liquid polysulfides from which the oxidized polysulfide polymers originate and which serve as reducing agents in the reclamation of the sealants according to this invention are polymers or oligomers having the structure HS—(RSS)$_n$—R—SH wherein R may be a hydrocarbyl, oxahydrocarbyl, or thiahydrocarbyl radical and n may be from 5 to 50. Preferably, the liquid polysulfides are polymers or oligomers of bis-(ethylene oxy) methane containing disulfide linkages and having terminal reactive mercaptan groups. Although branching is introduced into the polymer chain by the incorporation of small amounts of trichloropropane, the average structure of the preferred liquid polysulfide may be illustrated by the formula:

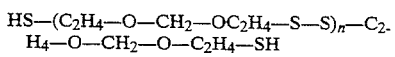

wherein the value of n, which governs the molecular weight of the polymer or oligomer, may be from 5 to 50. Preferably, the molecular weight of the liquid polysulfide is from about 400 to about 4000, more preferably from about 1000 to about 2000 or less. A range of liquid polysulfide polymers and oligomers is sold by Morton International, Inc. under the trademark LP. Several of these LP polysulfides are listed in Table 1 along with various characteristics of the materials.

TABLE 1

|  | LP-2 | LP-32 | LP-31 | LP-3 | LP-33 |
| --- | --- | --- | --- | --- | --- |
| Average Mol. Wt. | 4000 | 4000 | 8000 | 1000 | 1000 |
| n value | 23 | 23 | 42 | 6 | 6 |
| Mole % branching | 2 | 0.5 | 0.5 | 2 | 0.5 |
| % mercaptan | 1.5–2.0 | 1.5–2.0 | 1.0–1.5 | 5.9–7.7 | 5.0–6.5 |

In addition to the oxidized polysulfide polymers, in which there are substantially no residual mercapto groups, the cured sealant which is reclaimed for recycling by this invention comprises residual inorganic oxidizing agents such as manganese oxide ($MnO_2$), lead oxide ($PbO_2$), calcium peroxide, sodium perborate, and zinc peroxide; curing rate modifiers; fillers such as calcium carbonate, clays, and reinforcing carbon black; plasticizers such as chlorinated biphenyl and butyl benzyl phthalate; pigments such as titanium oxide; thixotropic agents; and residual latex stabilizers such as a sodium polyacrylate. Typically, the cured sealant contains from about 25 to about 50 weight percent of the oxidized polymer. The construction grades, including the window sealants, contain the highest level of fillers whereas the aircraft sealants have the lowest filler content but also contain adhesion promoters such as phenolic and silane resins. Scraps of the cured sealant generated by various applicators are the largest source of raw material for the method of this invention. The size of these scraps is not critical but smaller particles give rise to larger effective surface areas for reaction with the liquid polysulfides and thus the scrap may be milled and chopped, if necessary, to obtain particles of about one inch or less in each dimension.

A preferred level of mercapto group content in the reclaimed sealant is from about 1.5 to about 2.5% by weight. Because of the presence of residual oxidizing agents in the sealant to be reclaimed, the amount of liquid polysulfide to be mixed with the cured sealant must be increased over and above that which would provide the desired level of mercapto groups in the reclaimed sealant. The determination of the amount of residual oxidizing agent and calculation of the amount of extra liquid polysulfide is easily accomplished by those of ordinary skill in this art. Beyond that, the amount of liquid polysulfide necessary to provide the desired mercapto content in the reclaimed sealant may be calculated by dividing the desired mercapto percentage value by the percent mercapto group in a specific liquid polysulfide. Generally, the amount of mercapto group-terminated liquid polysulfide used is from about 10% to about 50% or more by weight of the cured, substantially mercapto group-free polysulfide in the sealant and preferred amount is about 40% or more.

The temperature for the reduction of the sulfide linkages in the cured sealant by the mercapto groups of the liquid polysulfide is preferably from about 75° to about 110° C. The time for the reduction may vary from about 0.5 hour to about 2 hours or more.

In the following examples, all parts are by weight unless stated otherwise.

EXAMPLE I

One hundred parts of a liquid polysulfide (LP-3) was heated in a resin flask to 95°±5° C. and 200 parts of a milled cured sealant was added gradually over a period of about 50 minutes and the temperature was maintained for an additional 1.5 hours. Upon cooling to room temperature, the resulting liquid had a Brookfield viscosity of 750 poise and an SH content of 1.6% by weight. This reverted material was cured again by adding 20.5 parts of a conventional curing paste comprising equal weights of manganese dioxide and Santicizer 278 plasticizer and 0.5 part per hundred of an accelerator to it and holding it at room temperature for 14 days. The tensile strength at break, maximum elongation, and Shore A hardness of this re-cured sealant were measured by the Instron Series IX Automated Materials Testing System at a sample rate of 9.10 pts/sec, a crosshead speed of 20 in/min, a full scale load range of 20 lbs., and an extensometer switch value of 1000% offset. The humidity was 50% and the temperature was 72° F. The Shore A hardness was 35.0 Durometer and the other values for 5 specimens of the re-cured sealant are given in Table 2.

TABLE 2

| Spec. No. | Tensile Str. (psi) | Ultimate elongation (%) |
| --- | --- | --- |
| 1 | 177.7 | 522.8 |
| 2 | 184.9 | 530.9 |
| 3 | 181.1 | 468.3 |
| 4 | 111.2 | 273.9 |
| 5 | 185.1 | 505.3 |

The subject matter claimed is:

1. A method for reclaiming a cured polysulfide sealant comprising mixing the sealant in a non-aqueous system at a temperature of from about 50° C. to about 100° C. with an amount of a mercapto-group terminated liquid polysulfide sufficient to provide from about 1.0% to about 3% by weight of mercapto groups in the reclaimed sealant.

2. The method of claim 1 wherein the temperature is from about 75° to about 100° C.

3. The method of claim 1 wherein the liquid polysulfide is an oligomer having a molecular weight of from about 400 to about 4000.

4. The method of claim 1 wherein the cured sealant comprises a residue of an oxide curing agent.

5. The method of claim 1 wherein the liquid polysulfide is from about 10 to about 50% of the weight of cured, substantially mercapto group-free polysulfide in the sealant.

* * * * *

UNITED STATES PATENT AND TRADEMARK OFFICE
CERTIFICATE OF CORRECTION

PATENT NO. : 5,349,091
DATED : September 20, 1994
INVENTOR(S) : Hallisy et al.

It is certified that error appears in the above-indentified patent and that said Letters Patent is hereby corrected as shown below:

Column 4, line 44   change "100°C" to --110°C--

Column 4, line 49   change "100°C" TO --110°c--

Signed and Sealed this

Fifteenth Day of November, 1994

BRUCE LEHMAN

Attest:

Attesting Officer    Commissioner of Patents and Trademarks